United States Patent [19]  [11] 4,244,803
Aladjem et al.  [45] Jan. 13, 1981

[54] QUANTITATIVE PROTEIN ANALYSIS BY IMMUNODIFFUSION

[76] Inventors: Frederick J. Aladjem; Padmasini K. Ayengar, both of 845 Las Palmas Rd., Pasadena, Calif. 91105

[21] Appl. No.: 97,931

[22] Filed: Nov. 27, 1979

Related U.S. Application Data

[60] Division of Ser. No. 29,772, Apr. 13, 1979, which is a continuation-in-part of Ser. No. 892,953, Apr. 3, 1978, Pat. No. 4,162,208, which is a division of Ser. No. 546,351, Feb. 3, 1975, Pat. No. 4,097,149.

[51] Int. Cl.³ ............ G01N 27/26; G01N 33/16; G01N 21/00
[52] U.S. Cl. ............ 204/299 R; 204/180 S; 204/180 G; 23/230 B; 424/12; 356/39; 356/72; 356/344
[58] Field of Search ............ 204/180 G, 180 S, 299 R; 23/230 B; 424/12; 356/72, 39, 402, 344

[56] References Cited

U.S. PATENT DOCUMENTS

| 3,096,137 | 7/1963 | Silard | 356/344 X |
|---|---|---|---|
| 3,553,067 | 1/1971 | Dwyer et al. | 204/180 S |
| 4,012,634 | 3/1977 | Bouton et al. | 356/39 X |
| 4,070,113 | 1/1978 | Frazer et al. | 356/39 X |
| 4,159,895 | 7/1979 | Shine | 356/39 X |

Primary Examiner—Arthur C. Prescott
Attorney, Agent, or Firm—Charlton M. Lewis

[57] ABSTRACT

Methods and apparatus are described by which immunochemical procedures such as immunodiffusion and immunoelectrophoresis can be used to provide quantitative measurement of the concentration of individual proteins in fluids such as serum, spinal fluid, tissue extracts and the like. That is accomplished typically by photooptically scanning the zones of precipitation which are produced, in parallel with those of standard preparations containing known concentrations of the proteins to be determined; deriving from the arrays of measurements of the precipitation zones selected parameters; and comparing the parameter values of the experimental and reference preparations. The zone measurements are preferably made and recorded electronically, with suitable digital manipulation of the resulting video values at a plurality of selected positions for each zone.

8 Claims, 14 Drawing Figures

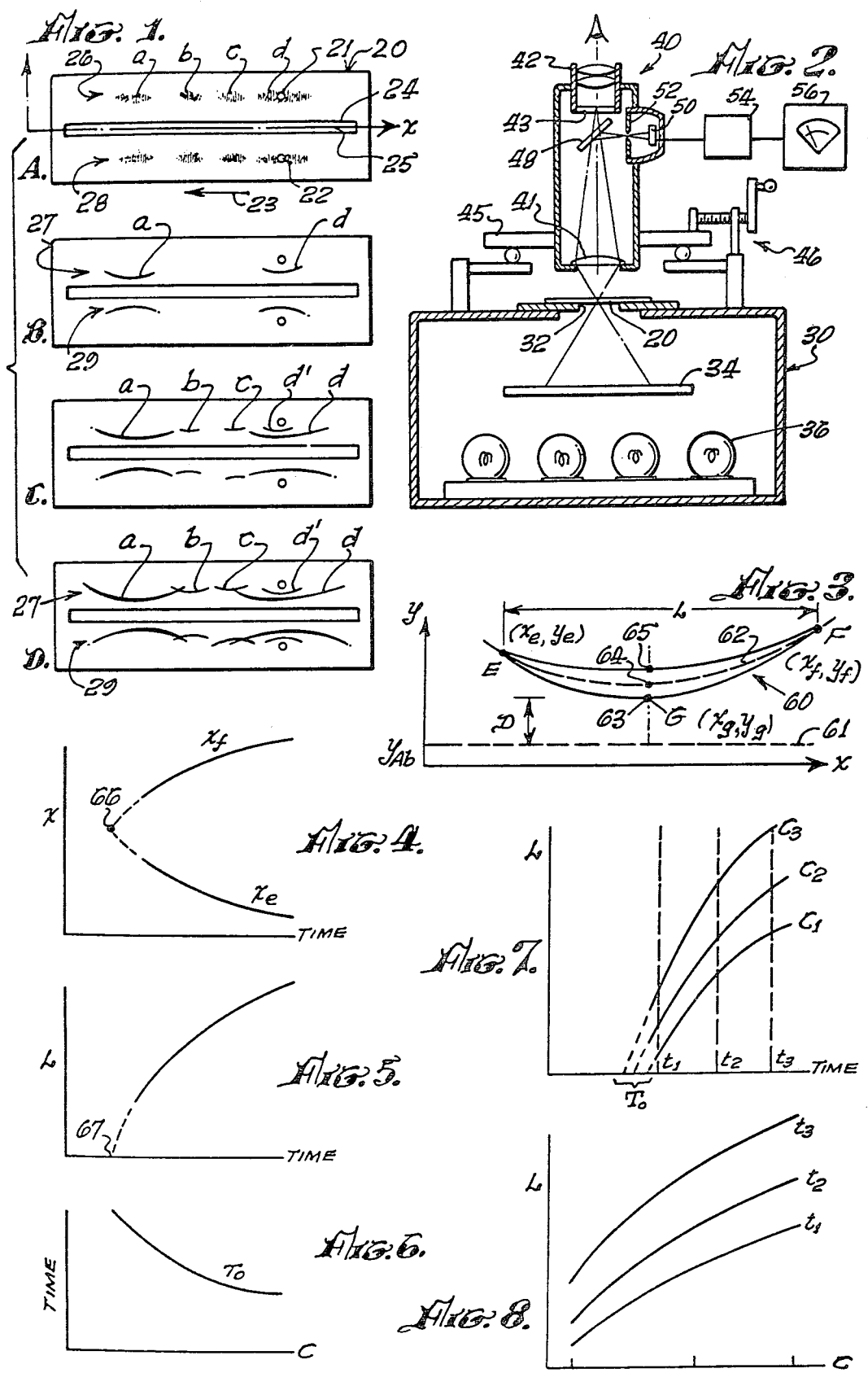

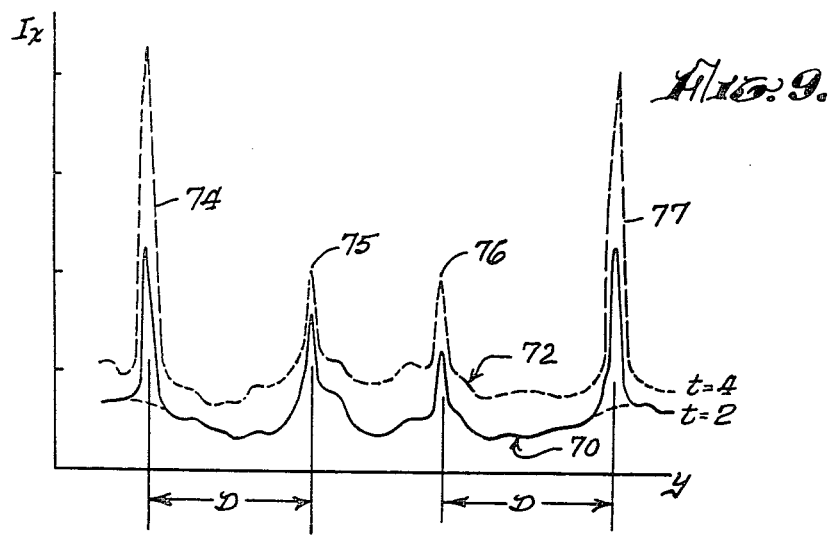
FIG. 9.
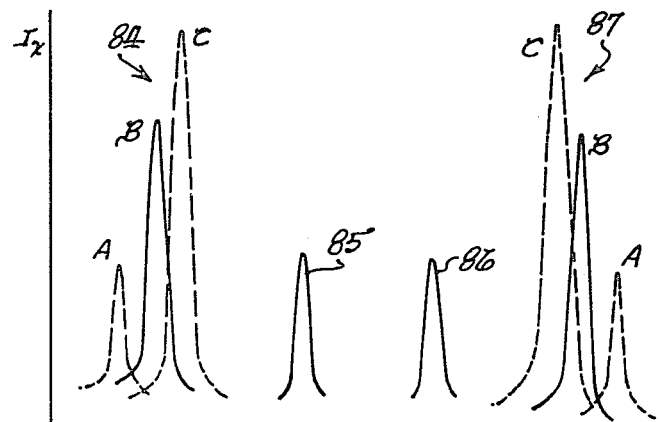
FIG. 10.
FIG. 12.
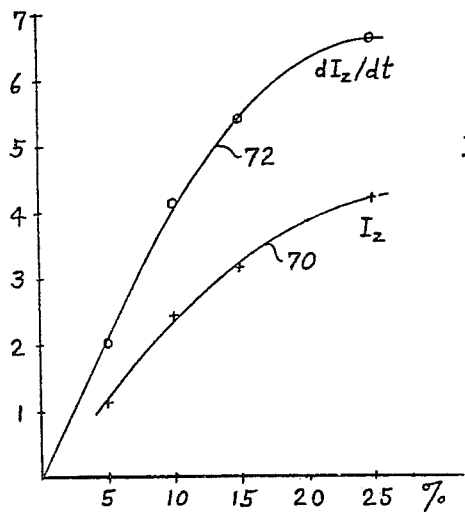
FIG. 11.
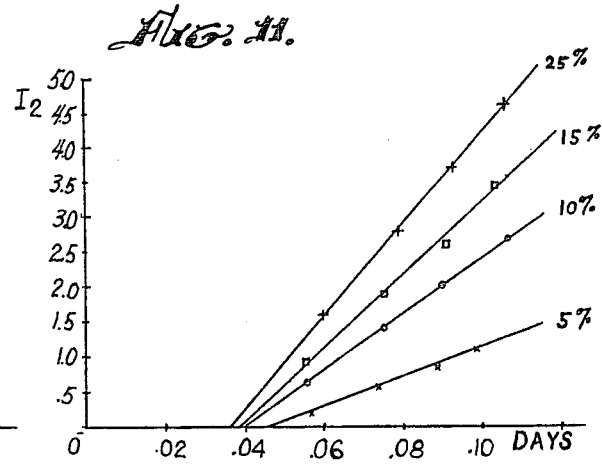

QUANTITATIVE PROTEIN ANALYSIS BY IMMUNODIFFUSION

RELATED APPLICATIONS

This application is a division of application Ser. No. 29,772, filed Apr. 13, 1979, which is a continuation-in-part of the copending patent application Ser. No. 892,953, filed Apr. 3, 1978, now U.S. Pat. No. 4,162,208, which is a division of application Ser. No. 546,351, filed Feb. 3, 1975, now U.S. Pat. No. 4,097,149.

BACKGROUND OF THE INVENTION

This invention relates generally to the quantitative measurement of proteins in mixtures, especially when only small amounts of material are available.

In view of the current rapid expansion of knowledge concerning the role of proteins in health and disease, there is an increasing need for a general, rapid and relatively economical quantitative method for protein analysis of such fluids as serum, spinal fluid, tissue extracts and the like.

The proteins occurring in such fluids are frequently identified by immunochemical procedures which depend upon precipitation of each protein by an antibody specific to the particular protein. The production of such specific antibodies is stimulated when foreign proteins (antigens) are introduced into a living body. Antisera can be prepared, containing known mixtures of such antibodies. By reacting a protein sample in vitro with such an antiserum and observing the resulting precipitation, or lack of precipitation, useful qualitative information may be obtained as to the types of proteins in the sample.

SUMMARY OF THE INVENTION

A primary object of the present invention is to obtain quantitative values for the concentration of one or more proteins in an antigen solution, utilizing immunodiffusion procedures which have previously been regarded as only qualitative techniques. That has been accomplished in large part by selecting suitable parameters for measurement and computation, and by providing adequate reference standards to which the results can be compared.

In preferred form of the invention, the proteins in the initial antigen mixture are first partially fractionated by causing them to migrate in one dimension at rates that differ characteristically among the various proteins. Such selective migration may, for example, utilize simple diffusion, electrophoresis, or more complex techniques such as chromatography. In the illustrative case of electrophoresis, differences of electrophoretic mobility between different proteins cause the proteins to become distributed in the direction of the electrical field in accordance with their mobility. Following such initial fractionation, the resulting essentially linear distribution of proteins is brought into contact with the antiserum by relative movement in another dimension, typically by mutual diffusion in a suitable agar or agarose support medium. The precipitation zones of the respective proteins are then typically entirely separate and can be clearly distinguished. That overall process, known as immunoelectrophoresis, is well recognized as a qualitative method of great power and flexibility for detecting the presence or absence of certain antigens or the antibodies against them.

Useful separation of the precipitation zones of a plurality of distinct proteins is also attainable without an initial step of fractionation, if the antigen and antibody are allowed to diffuse toward each other in a manner to form elongated precipitation zones of limited length extending transversely of the primary direction of diffusion. The mobilities for diffusion of different proteins, and/or of their antibodies, are ordinarily sufficiently different that such precipitation zones are clearly distinguishable. Any overlapping that may occur is usually limited to portions of the zones, the zone end points being usually clearly separated. The quantitative procedures of the present invention are usefully applicable to immunodiffusion of the described type.

Similarly, if antigen and antibody are placed into wells for immunodiffusion, and an electric field is applied to accelerate the movement of the antigen and antibody toward each other, as in the procedure known as electroimmunodiffusion, the resulting precipitate zones retain the same basic forms as in absence of an electric field. The same is true if the immunodiffusion step of immunoelectrophoresis is aided by a suitably directed electric field. Accordingly, the term "immunodiffusion" in the present specification and claims refers to diffusion with or without an accelerating electric field.

In accordance with one aspect of the invention, a large number of measurements are carried out in a systematic manner as the precipitation pattern develops, and the resulting direct data are then employed for deriving values of carefully selected and relatively specific parameters of individual selected precipitation zones. Those parameter values are compared with values obtained under comparable conditions from a series of standard or reference runs which have been suitably selected and treated to facilitate reliable interpolation. That procedure has been found to yield satisfactorily consistent and reproducible quantitative values for the actual concentrations of the selected proteins in the sample.

The described collection of initial experimental data and the computations made with them can be carried out manually, if desired. They are also well adapted for semi-automatic data collection by optical and electronic scanning devices. Also, the necessary data processing can be made fully automatic by use of a general purpose computer of moderate capacity. Such automated operation permits collection and processing of ample data for calculating results from several independent sets of data or by use of more than one parameter or group of parameters, thereby providing a basis for estimating reliability, as by computing probable errors.

A further aspect of the invention employs comparisons of concentration values obtained from different parameters, or evaluation of parameter values themselves, as a means of detecting presence of certain protein abnormalities.

The invention further may utilize the same optical sensing system for scanning the precipitation zones and for initially locating and identifying the reactant wells for automatically depositing selected reactants in them.

BRIEF DESCRIPTION OF THE DRAWING

In the following description of certain illustrative manners of carrying the invention into practice, reference well be made to the accompanying drawings in which:

FIG. 1 is a schematic plan of an immunoelectrophoresis plate, FIG. 1A illustrating a typical distribution of proteins following electrophoresis, and FIGS. 1B, 1C and 1D illustrating successive stages of the subsequent diffusion and immunoprecipitation reaction;

FIG. 2 is a schematic axial section representing typical apparatus for measuring a slide;

FIG. 3 is a schematic drawing illustrating properties of a precipitation zone relating to the invention;

FIG. 4 is a graph representing typical dependence of zone end points upon time;

FIG. 5 is a graph representing typical dependence of zone length upon time;

FIG. 6 is a graph representing typical dependence of time of initial zone appearance upon protein concentration;

FIGS. 7 and 8 are graphs representing typical dependence of zone length upon time and upon protein concentration;

FIG. 9 is a graph showing actual intensity scans across a precipitation zone at two incubation times;

FIG. 10 is a graph representing intensity scans across precipitation zones formed by respective protein concentrations;

FIG. 11 is a graph representing illustrative dependence of the parameter $L_z$ upon time;

FIG. 12 is a graph representing illustrative dependence of the parameter $I_z$ and of the parameter $dI_z/dt$ upon protein concentration;

DESCRIPTION OF ILLUSTRATIVE EMBODIMENTS

Figure 13:
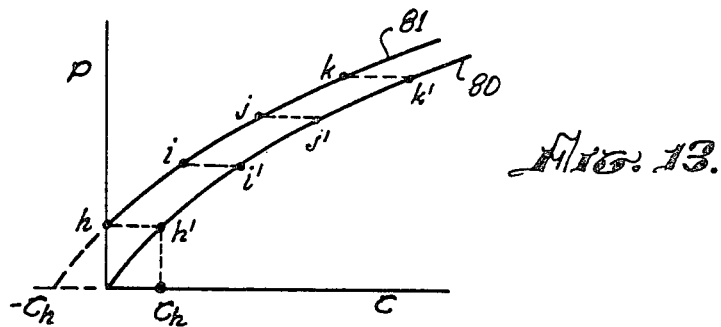
FIG. 13 is a schematic graph illustrating derivation of protein concentration values by known additions of the protein to the unknown sample.

Many aspects of the invention are well illustrated by its embodiment in the preferred process of immunoelectrophoresis, and the following description will emphasize that form of the invention, but without implying any limitation of scope.

Immunoelectrophoresis is well known as a qualitative procedure, and many forms of apparatus have been described for carrying it out, differing in detail rather than in principle. The electrophoresis and subsequent diffusion and immunoreaction are typically performed in a single layer of gel from a fraction of a millimeter to several millimeters thick carried on an optically transparent sheet. A currently preferred supporting medium is agarose saturated with barbital buffer of approximately pH 8.6 and ionic strength 0.1. The active materials are typically inserted into wells, which may be cut from the gel coating or formed when the gel is molded on the carrier.

FIG. 1 shows schematically a plate 20 with a typical arrangement of wells, comprising the two circular antigen wells 21 and 22, spaced equally on opposite sides of the elongated antibody well or trough 24 with axis 25, which extendss parallel to the direction of electrophoresis. With that geometric arrangement of wells two distinct antigen solutions, or two specimens of the same solution, can be run simultaneously against the same antibody solution on each plate. If preferred, the capacity of each plate can be multiplied, as by providing additional antibody wells outward of the two illustrated antigen wells, with additional antibody wells outward of them. Similarly, additional antigen wells may be added, spaced far enough from wells 21 and 22 in the direction of electrophoresis to prevent overlapping of the patterns.

The shaded areas 26 and 28 in FIG. 1A represent typical approximate distributions of four varieties of protein a, b, c and d from duplicate samples in the respective wells 21 and 22 following a period of electrophoresis in the direction of the arrow 23. Although all proteins usually migrate in the same direction through the liquid medium, the solvent itself tends to carry a net charge and to have a resultant flow or electroosmosis relative to the gel. Hence the proteins may have a net movement in either direction relative to the well.

Following termination of electrophoresis and addition of antibody solution to well 24, precipitation zones are produced by mutual diffusion of the proteins a, b, c and d of FIG. 1A and the corresponding antibodies. FIGS. 1B, 1C and 1D show typical zones at respective stages of development.

The precipitin arcs of unrelated antigens, reacting with the antibodies against them, form independently, and may cross when they are sufficiently close together, as shown in FIG. 1D; whereas the arcs of antigens that are immunochemically related typically join in a continuous reaction. The zone of precipitation d' in FIGS. 1C and 1D indicates that the area d of FIG. 1A actually contained two distinct proteins, illustrating the fact that even antigens which have identical electrophoretic mobility may form distinct zones of precipitation. The zones d and d' may alternatively be viewed as representing two distinct proteins that were initially placed in well 21 and were subjected to immunodiffusion without initial electrophoresis. The clear separation of the respective zone ends would then be due to different rates of diffusion of the proteins or of their antibodies. In either case, each such zone can be analyzed independently, using any or all of the methods of analysis to be described.

In accordance with the present invention, the zones of precipitation resulting from immunoelectrophoresis are subjected to direct quantitative measurements. Such measurements may determine only the physical position on the plate of certain selected features of each precipitation zone of interest, or may include quantitative photooptical measurements of the light intensity. For both types of measurement, the time is noted and may be used as an integral part of the observational data. If the incubation process is allowed to reach equilibrium, producing a nearly static zone configuration, the exact time of measurements becomes immaterial.

Position measurements on slide 20 can be made, for example, with the aid of a low power microscope. As represented schematically in FIG. 2, plate 20 is placed over an adjustable opening 32 in the top of a light-tight box 30 with the lamps 36 and the dark backing 34 of light absorbing material such as black velvet. The microscope 40 has the objective lens 41, the eye piece 42 and a set of cross hairs or other reference reticle at 43 in the focal plane. The microscope is mounted above light box 30 on a double slide mechanism 45 with screw drive 46, and with accurate scales, not explicitly shown, for reading the microscope position in two coordinates. For clarity, only one coordinate of the movement is directly indicated in the drawing. It is usually convenient to select coordinates having the x-axis, say, parallel to the direction of electrophoresis and to the length of the antibody well, and having the origin of coordinates at or near the well axis 25, as indicated in FIG. 1A.

For measurements of the light intensity the microscope typically includes an oblique beam-splitting mirror 48 which sends part of the light to the eye piece while another part forms a real image in the plane of a diaphragm 52. Diaphragm 52 then transmits to the photosensitive transducer 50 only radiation from the elemental area of plate 20 that coincides optically with the cross hair image. Transducer 50 is electrically connected to the amplifying circuit 54 and the meter 56. The latter may be observed visually and the value recorded manually, or the meter may embody means such as analogue-to-digital circuitry and printout mechanism for automatically recording the light intensity in response to a command signal. Many changes can be made in the illustrative apparatus of FIG. 2, including, for example, replacing the dark field illumination by direct lighting or by top lighting such that light reflected from the zone is observed or measured. Illustrative apparatus for making completely automated measurements is described below.

FIG. 3 illustrates schematically certain preferred precipitation zone features which are selected by the present invention for position measurement as the zone develops. The horizontal line 61 at $y = y_{Ab}$ represents the adjacent edge of the antibody well in the immunoelectrophoresis slide. The points E and F at the coordinates $(x_e, y_e)$ and $(x_f, y_f)$ respresent the left and right end points of the elongated zone 60.

In addition to the zone end points E and F, we have found it useful to measure coordinates of a number of intermediate points of each zone. The single point G at the coordinates $(x_g, y_g)$ in FIG. 3 is illustrative of such points.

Since the zone has some width in the y direction, the y coordinate of each intermediate point such as G can be conveniently placed either at 63 at the leading edge of the zone closest to the antibody well, at 65 at the trailing edge of the zone, or at one or more points such as 64 within the zone, typically including the point of maximum intensity.

As the zone develops with increasing time of incubation, the points E, F and G progressively change both their relative and their absolute positions. Illustrative values of $x_e$ and $x_f$ as functions of time are plotted in FIG. 4 for a typical protein concentration. Such position values may be used directly for determining protein concentration, as by comparing the values of $x_e$ and $x_f$ obtained with unknown solutions to corresponding values obtained with known concentrations of proteins at measured times. However, more reliable and accurate results are ordinarily obtainable by deriving from such initial measurements one or more functions, which will be referred to for convenience as parameters.

An important parameter of the precipitation zone employed by the present invention is the coordinate difference $x_f - x_e$, which is a measure of the length L of the precipitation zone at the particular time t of measurement. The variation of that parameter with time of incubation is plotted in FIG. 5 for the typical data of FIG. 4.

Position parameters other than the zone length L may be computed from measurements of the zone as it develops. For example, the zone curvature and its variation along the length of the zone are useful parameters, as well as providing information as to presence of protein abnormalities (see below). A rough measure of curvature for the zone arc as a whole, or for a selected zone segment, can be obtained by relatively simple comparisons of the x and y coordinates for three mutually spaced points on the zone axis. To obtain more accurate values of zone curvature, the zone axis is typically fitted approximately by a curve of the type $y = f(x)$, where $f(x)$ may represent any suitable function of x. The radius of curvature R is then given by the general formula $$R = \frac{y''}{[1 + (y')^2]^{3/2}} \quad (1)$$

where $y'$ and $y''$ represent the first and second derivatives of y with respect to x.

A suitable illustrative function for curve fitting represents a parabola, typically with axis parallel to the y axis. Such a parabola may be expressed in either of the equivalent forms $$y = a_0 + a_1 x + a_2 x^2 \quad (2a)$$

and $$y = A(x - B)^2 + C \quad (2b)$$

where $$A = a_2 \quad B = -a_1/2a_2 \quad C = a_0 - a_1^2/4a_2$$

The values of the constants in (2a) or (2b) can be found directly from the coordinates of any three points of the zone axis, or may be fitted by least squares or other known procedure to any desired number of such points. The axis of symmetry of the parabola is at $x = B$, and the curve at that axis is a distance C from the x axis. Using the formula (1), the radius of curvature may be expressed as $$R = \frac{2A}{1 + [4A^2(x - B)^2]^{3/2}} \quad (3)$$

That radius has its maximum value $R_o$ at the axis of symmetry, where (3) reduces to $$R_o = 2A \quad (4)$$

Any of the above quantities, which may be derived as indicated from as few as three points of the zone axis, may be employed as parameters in accordance with the invention.

Another parameter that is useful for determining protein concentration in accordance with the invention is the time $T_o$ of first appearance of the zone. That time is difficult to determine by direct observation. One aspect of the invention provides a practical way of obtaining a reliable and reproducible value for the time of first appearance.

In FIGS. 4 and 5 the solid lines represent typical plots of direct experimental values. The figures also include extrapolations of the solid curves toward earlier times. The extrapolations are shown as dashed lines. The point 66 at which the extrapolated curves of FIG. 4 meet represents a time at which the zone must have had zero length. The extrapolated curve of FIG. 5 intersects the time axis at the point 67, giving an equivalent procedure for finding $T_o$. Such extrapolation represents a reasonable and highly useful definition of the time of first appearance of the precipitation zone. That method of determining $T_o$ has the advantage that continuous observation of the plate is not required.

Turning now to the quantitative determinations of the zone light intensity, it has been discovered that a single light intensity reading does not usually provide a useful measure of protein concentration. That is primarily due to the variability of zone shape and speed of formation, and the tendency of the intensity to change as the zone expands.

On the other hand, we have found that the variability of such factors can be largely compensated by taking a series of intensity readings at suitably selected locations and treating them collectively to evaluate an intensity parameter. A preferred procedure is to take such readings at uniform intervals along a line extending linearly across the zone of precipitation, typically in the y direction at a particular value of x. Such a series preferably includes several intensity values outside of the zone at each side. Those offset values are then averaged to provide a measure of the background intensity, which is subtracted from each of the intensity readings within the zone. The resulting adjusted intensity values are effectively summed, yielding essentially a linear integral of the intensity along a line crossing the zone at a selected value of x. We have found that such a linear intensity sum $I_x$ tends to increase with incubation time in a regular and reproducible manner, the value at any given time increasing with the concentration of the reacting protein over a wide range of experimental conditions.

Typical plots of the relative intensity observed during cross-zone scans are shown in FIG. 9. The two curves were plotted by semi-automatic apparatus of the type described below, scanning in the y direction at $x_g$, the point of closest approach of the precipitation zones to the antigen well. The peaks at 74 and 77 in FIG. 9 are due to the zones formed on opposite sides of an antibody well by identical protein samples in the two antigen wells of a plate similar to that of FIG. 1. The two small peaks at 75 and 76 are due to the respective edges of the antibody well, providing a convenient reference from which to measure distances such as D from selected zone points to that well. The parameter $I_x$ defined above corresponds essentially to the area under a peak such as those at 74 or 77 of FIG. 9.

Peaks 74 and 77 of FIG. 9 were made with identical samples of human serum albumin. They illustrate typical development of the precipitation zones between 2 hours of incubation (solid line curve 70) and 4 hours (dashed line curve 72). Although the zone position remains remarkably stationary during the time between those two sets of measurements, the area of each peak grows appreciably. The near identity of the peaks at 74 and 77 is noteworthy. The two curves are offset vertically by an arbitrary distance for clarity of illustration.

FIG. 10 is a schematic plot illustrating typical scans in the y direction on plates made with different concentrations of protein, all measured at substantially the same time of incubation. The graph brings out clearly the increasing area of the individual peaks and the shift of the entire zone toward the antibody well with increasing protein concentration progressing from peaks A to C.

Whereas the parameter $I_x$ is highly useful for determining protein concentrations, still better results are obtained from a multiple intensity parameter, obtained by summing or averaging such linear intensity sums at several different x values. A typical procedure is to compute linear sums at $x_g$ and at values spaced on each side of $x_g$ by a selected interval. Averaging or summing a uniform predetermined number of such linear sums reduces experimental error and improves the overall accuracy of the determination of protein concentration.

In accordance with another, generally preferred procedure, each time the plate is scanned the number of linear sums included in the computation is increased as the length of the precipitation zone increases. An illustrative procedure of that type is to determine the linear sum of the intensity at $x_g$ and to continue to compute such sums on each side of $x_g$ until the value of the sum falls below a selected threshold. Addition of all the linear sums provides a parameter $I_z$ which is essentially the integral of the intensity of the zone of precipitation at the time of the scan. That approximation can be obtained as precisely as is desired, within the limits of resolution of the instrumentation, by reducing the x and y increments at which measurements are made. The value of $I_z$ varies especially steeply as a function of protein concentration over a wide range of experimental conditions. That is because, as the concentration is increased, both the x and y dimensions of the zone increase, and the average intensity of the zone also tends to increase. That steeper dependence upon protein concentration makes the total intensity parameter especially effective as a criterion for determining the concentration.

After obtaining experimental values for one or more parameters for an antigen sample to be analyzed, those values are compared with suitable sets of standard values for the respective parameters, obtained under closely similar experimental conditions but with a series of protein solutions containing respective known concentrations of the protein of interest. To obtain such an array of standard values, standard runs are carried out with such standard protein solutions, and measurements are made at corresponding points of the respective plates at successive times as their incubation proceeds. The standard runs are preferably carried out with all conditions as nearly identical as possible to those of the experimental runs for which they are to provide reference values. In fact, a distinct set of reference values is preferably obtained for every group of experimental runs. However, for routine measurements for which the reference curve slopes are known from previous experience, even a single standard run may sometimes suffice.

Standard values of the selected parameter are derived from the results of those standard measurements, typically for each concentration and at several times. Each measured standard value of the parameter is therefor considered as a function of both concentration and time. When individual linear intensity sums $I_x$ are to be considered separately, a full identification also requires specification of the value of x.

An advantage of using the time of first appearance of the zone as a parameter is that standard values of $T_o$ do not involve time as a variable. That is, although the evaluation of $T_o$ by the methods described requires measurements at a series of definite times, once $T_o$ has been derived from those measurements the times of the respective measurements become immaterial. Thus, the values of $T_o$ can be plotted as a function of protein concentration C, yielding a single standard curve. Such a curve is represented schematically in FIG. 6, typically based on values obtained for respective concentrations by the extrapolation method described in connection with FIGS. 4 and 5. Concentration values are directly readable from the curve of FIG. 6 for an unknown sample once its $T_o$ has been measured.

In the case of parameters such as L, $I_x$ and $I_z$ preparation of standard curves may be less direct. Since values depend upon the times at which the measurements are made, the series of reference standards must be prepared in such form that they cover a range of times. It is not always feasible to measure data for all concentrations at the same moment. Each measured value is therefore associated with its time of measurement, and the resulting standard values for the respective protein concentrations are then plotted on separate curves as functions of time.

FIG. 7 shows a typical family of such curves in which standard values of the parameter for three concentrations are plotted against time. It is noted in passing that the indicated extrapolation of those curves to $L=0$ can provide standard values of $T_o$ for plotting FIG. 6, or can provide experimental values of $T_o$ for comparison with FIG. 6. Vertical lines are drawn on FIG. 7 at a series of arbitrary times, shown as $t_1$, $t_2$ and $t_3$. Their intersections with the curves then provide a set of L values for different concentrations, all corresponding to the same time. Each such set of L values is replotted as a separate curve as a function of concentration. The result is an array of curves, each showing L as a function of protein concentration for a particular time. Such an array is shown schematically in FIG. 8, and is found more convenient for comparison with an experimental parameter value than the plot against time of FIG. 7.

Standard values for comparison with experimental values of other parameters are typically obtained and treated in a manner analogous to that described for the parameter L.

We have discovered, however, that the total intensity parameter $I_z$, when measured for given protein concentration at successive times of zone development, increases linearly with the time. That linear relation is illustrated in FIG. 11, which is a plot of $I_z$ against time for four solutions containing the indicated known concentrations of the protein immunoglobulin. The indicated values of $I_z$ were derived by a suitably programmed general purpose computer from intensity values measured automatically at a two-dimensional array of zone poositions in the general manner to be described. The points shown in FIG. 11 were originally plotted automatically, and the straight-line curves were fitted to each set of points, by the computer. The figure has been redrawn manually and is reproduced at greatly reduced scale.

The linear relation shown in FIG. 11 aids the preparation of standard or reference plots from which to read the protein concentration corresponding to an experimental value of the parameter $I_z$. One such curve, derived from the data of FIG. 11 and showing $I_z$ as a function of concentration for the time 2.4 hours, is shown in FIG. 12 at 70.

The linear dependence of $I_z$ upon time also means that the time derivative $dI_z/dt$, or rate of change of $I_z$ with time, is constant. It thus provides a parameter having the practical advantage that it does not depend upon time. Curve 72 in FIG. 12 illustrates typical behavior of that parameter as a function of protein concentration, each point representing the slope of one of the curves of FIG. 11. As already explained in connection with the parameter $T_o$ and FIG. 6, a single curve such as 72 of FIG. 12 can serve effectively as reference curve for the parameter $dI_z/dt$.

A further aspect of the invention provides improved accuracy, especially when the sample under study contains the protein or proteins of interest at relatively low concentrations. The standard solutions are then preferably supplemented by adding known amounts of such proteins directly to aliquot portions of the sample itself, and running the resulting solutions in parallel with the original solution, and with standards containing definitely known concentrations of the protein. Values are obtained for the desired parameter for the respective solutions all at a uniform time, using the above described technique for interpolating with respect to time if necessary. The parameter values P obtained for the regular standard solutions are plotted against protein concentration in the usual way, as indicated schematically by curve 80 in FIG. 13. Also plotted are the values of P for the original antigen sample, and for the portions of that sample to which protein was added in known amount, indicated typically as the respective points h, i, j and k. Those points are plotted relative to the horizontal concentration axis as if the solutions contained only the protein that was added. Thus the value h for the original sample is plotted at $C=0$. Curve 81 is drawn through those points. With that illustrative arrangement of the data, the protein concentration in the original sample can be evaluated in several ways, which should give essentially the same value. Thus, any desired number of those procedures may be used, and the resulting values averaged.

First, horizontal projection from point h to intersect curve 80 at h' yields the concentration value indicated at $C_h$, which corresponds to the general comparison procedure previously described. Further, similar projection of each value i, j and k to intersect curve 80 provides a measure of the concentration in terms of the lengths of the lines from i to i', j to j' and k to k', all of which lengths are theoretically equal. If the value of P at he is somewhat uncertain, for example because the observed zone is faint, an average of all four intervals gives a more reliable value.

Another procedure has the advantage that it can not only improve the accuracy of an uncertain determination of h, but can also provide an answer even if the original sample contains less than the threshold value of protein needed to produce a measurable precipitation zone. In the latter case, the upper portion of curve 81 is drawn through the available points i, j and k, and is extrapolated to the P axis, thus providing a determination of P at h. In thus projecting curve 81, standard curve 80 is a helpful guide. For example, curve 80 is shifted bodily to the left in FIG. 13 till it represents as well as possible the points i, j and k. The intersection of the shifted curve 80 with the P axis then gives a good measure of point h, from which the concentration $C_h$ is found. Also, further extrapolation of curve 81 to the negative C axis at $-C_h$ gives a direct reading for the concentration, which should agree with the value $C_h$.

The described reliance upon the supplementary standard curve 81 has the great advantage of using the identical medium for the experimental and reference solutions. Especially when that medium is the human serum of a particular patient, that advantage more than overcomes any possibility of slight error in extrapolating the standard curve. By increasing the number of different amounts of added protein, the three shown illustratively in FIG. 13 being merely illustrative, and by using several runs for each amount, the reliability of the extrapolation can be increased almost without limit, and a good indication can be obtained of the experimental error that it may involve.

The invention further provides methods for the automated detection of abnormalities of certain proteins in an antigen sample. Normal and abnormal gamma globulin, for example, typically have slightly different ranges of electrophoretic mobility, but react with the same antibody, leading to precipitation zones with irregular and typically unsymmetrical distribution of precipitate along the length of the zone. Such irregularity can be detected by comparing experimental values of the intensity parameter $I_x$, for example, for different values of x. Observation of unsymmetrical or otherwise irregular variation of such values indicates that an abnormality has been encountered; and that indication is greatly strengthened if several independent determinations are carried out at each x value and if the computed experimental errors show the variation to be statistically significant.

That method may be considered as a special case of the general procedure of comparing the experimentally obtained values of different parameters which tend to respond differently to the abnormality of interest. For some parameters with such behavior it may be more effective to compare the values of protein concentration that correspond to the respective observed parameter values, rather than directly comparing the parameter values themselves. For example, the described irregular intensity distribution along the zone in presence of abnormal gamma globulin tends to cause the zone to appear sooner than normal, leading to higher values of computed concentration; whereas the total intensity parameter $I_z$ tends to yield approximately equal concentration values for the normal and abnormal proteins. Thus significantly poor agreement between concentration values obtained with $T_o$ and with $I_z$ indicates presence of abnormal protein.

A further parameter which responds sensitively to presence of abnormal protein is the curvature of the longitudinal axis of the zone. In presence of abnormality the curvature tends to vary irregularly and unsymmetrically along the length of the zone, while the overall curvature tends to be less than normal.

Further advantages are nearly always obtainable by employing multiple parameters which comprise specific functions of two or more parameters, such as the described position or intensity parameters. For example, the sum of the zone length L and an intensity parameter, each appropriately weighted according to its experimental error of measurement, provides a new parameter which tends to give more reliable results than either one of its components when used alone.

Another advantageous combination comprises a differential function of two parameters, one of which increases with increasing protein concentration, while the other decreases. Thus, a quotient or a difference of such parameters provides a multiple parameter with a steeper dependence upon concentration than either of its components. The time $T_o$ of first appearance of the zone is an example of a parameter having inverse relation to protein concentration, and is especially useful for constructing such quotients. The distance from the antibody well to the zone at any desired value of the x coordinate, for example the distance of closest approach at $x_g$, also depends inversely upon the concentration and may be employed as a parameter in such quotients. It is generally preferred to divide the parameter with direct dependence upon concentration by that with inverse dependence, so that the resulting multiple parameter has a direct rather than inverse net dependence.

Suitable reference values for comparison to experimentally determined multiple parameters of unknown samples are typically derived from reference values obtained as already described for the respective component parameters.

Whereas the position and intensity measurements and the parameter derivations that have been described can be carried out by direct visual and manual operations, as has been indicated, an advantage of the invention is that those operations are particularly well adapted for partial or substantially complete automation.

An especially convenient and effective procedure for making the measurements required by the invention is to scan the slide by optical means, such as a television camera, a charge coupled scanning device or equivalent means, for producing a video signal representing the apparent brightness of the scanned image at a two-dimensional array of elemental areas. That signal for each element is typically converted to digital form and electronically stored in association with signals representing the x and y corrdinates of the corresponding position on the plate and the time of observation. The entire array of such position signals, or the signal for a designated position, can then be recovered from memory as needed for further processing. Also, any desired portion of the slide image can be displayed either during the scanning operation or at a later time by means of a cathode ray tube or equivalent display device. Systems for scanning, storing and reproducing an image, and for extracting a video signal in digital form for a selected image point are well known in the electronic art, and are available commercially in forms well adapted for the present purpose.

Figure 14:
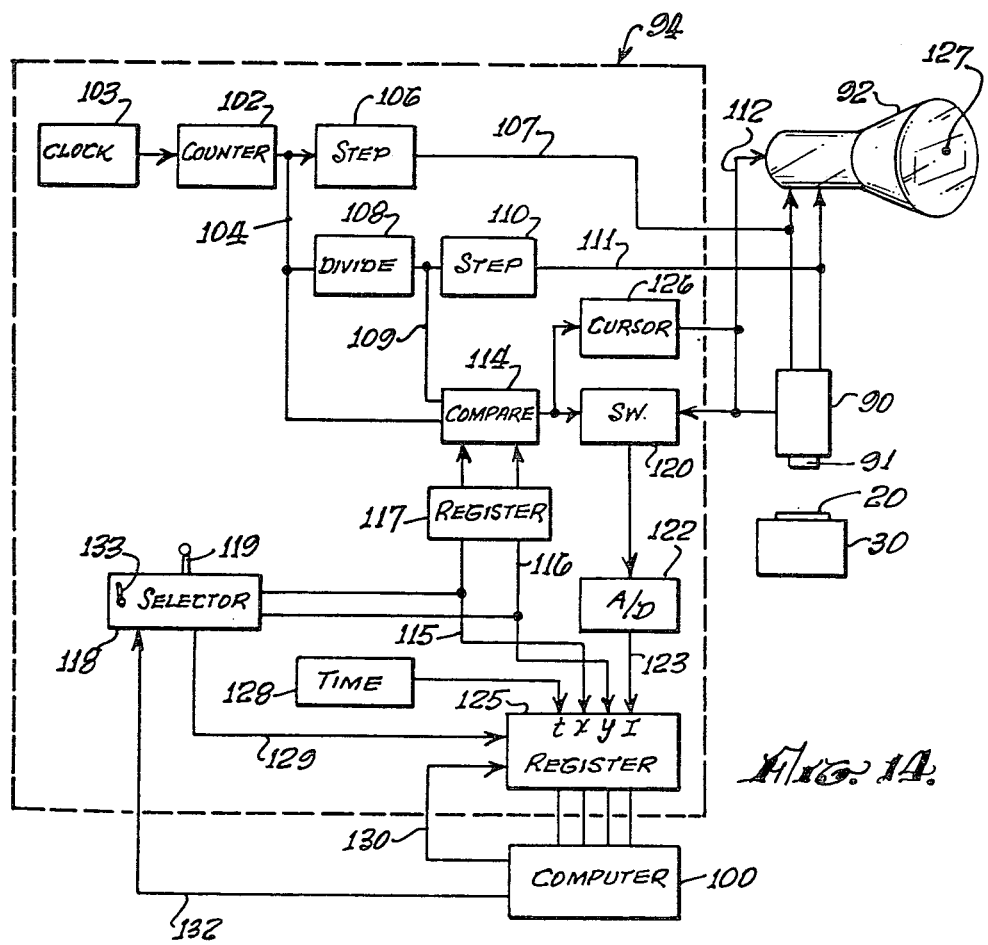
FIG. 14 is a schematic block diagram representing electronic scanning apparatus for carrying out the invention.

FIG. 14 represents schematically such apparatus in illustrative form, comprising the television camera 90 with lens 91 for imaging the plate 20 on the photosensitive surface of the camera, the monitor cathode ray tube 92, the scan control apparatus 94 and the general purpose computer 100. Plate 20 can be imaged at any desired magnification by conventional adjustment of lens 91. A desired portion of the plate can be centered in the field by shifting its position on its illuminated support, such as light box 30 of FIG. 2, or by conventional electronic bias controls in the camera circuits.

More particularly, the scanning movements in the scanning device and in the synchronized monitor cathode ray tube, if used, are typically driven stepwise in both coordinates, with steps so small that the movement appears virtually continuous on the screen. The image is thereby divided into elemental areas, which can be identified, for example, by specifying their x and y coordinates. For manual or semi-automatic operation, the monitor display typically includes a cursor comprising an electronically produced bright spot which designates on the screen the elemental area from which the video sample is being extracted once each complete scan. The operator is provided with manually controlled electronic switching means by which he can move the cursor about on the screen under visual control. Means may also be provided for directly placing the cursor at a desired point, typically in response to x and y signals in digital form constituting a command address. Such signals may be derived under manual control, or supplied from a computer in response to conventional program instructions.

As illustratively shown in FIG. 14, the counter 102 counts pulses received from the clock 103, producing on the multiple lines 104 digital signals which represent successive x coordinate values, say. Circuit 106 develops on the line 107 an analogue step voltage in response to those signals, with a step corresponding to each elemental x value. The dividing circuit 108 effectively counts the beam sweeps in the x direction, producing on the multiple lines 109 digital signals representing the y coordinate for each sweep. Circuit 110 develops on the line 111 an analogue step voltage in response to that count, with a step corresponding to each elemental y value. The step voltages on lines 107 and 111 control the x and y sweep movements in camera 90 and tube 92, insuring their synchronization. The video signal from camera 90 is supplied via the line 112 to monitor tube 92, reproducing on the tube screen the brightness variations of slide 20.

The selection circuit 118 typically comprises x and y counters which are selectively shiftable up or down either by a single counter or in a continuing series of counts in response to manual movement of the joy stick indicated schematically at 119. The resulting digital signals, representing x and y coordinates of a point selected for exploration, are stored in register 117. The comparison circuit 114 continuously compares the coordinates of that selected exploration address from register 117 with those of the scanning beams from lines 104 and 109. When the scanning spot reaches the stored address, typically once during each complete scan, comparison circuit 114 supplies an enabling pulse to the switching circuit 120. The video signal from camera 90 is thereby transmitted to analogue-to-digital circuit 122. The register 125 thus receives on the lines 123 a digital representation of the brightness of the scanned slide 20 at the selected exploration point. The enabling pulse from circuit 114 is supplied also to the cursor control circuit 126, superimposing upon the video signal a beam intensifying pulse which identifies that selected point on the monitor screen, as indicated schematically at 127.

Register 125 also receives the x and y coordinate signals from lines 115 and 116 and a digital signal continuously representing the time, developed under clock control by the time circuit 128. All of those signals are typically stored in register 125 for delivery to computer 100 in response to unload signals which may be supplied either under manual control via the line 129 from selector 118 or via the line 130 under control of the computer.

Computer 100 is preferably provided with means for independently designating an exploration address and thus obtaining input information for the spot of plate 20 that corresponds to specific requirements of any program under which it is operating. Such exploration means may comprise circuitry basically similar to selector 118, register 117 and comparison circuit 114, the selector operating in response to electronic signals which selectively indicate the required direction of movement of the exploration spot or the digital address of its required position. Rather than duplicating such apparatus, FIG. 14 indicates computer control of selector 118 by electronic signals supplied via the multiple lines 132, supplanting joy stick 119 when the switch 133 is shifted from manual position to automatic. With such control available the computer is readily programmed to carry out position and intensity measurements and parameter derivations of the general types that have been described.

For automatic scanning of zones, the plates of a set may be transferred in sequence from the incubation chamber to an accurately defined scanning position with suitable illumination. Especially when the optical scanning means is both light in weight and compact, as in the case of a charge coupled device, for example, it is generally preferred to mount that scanning device on a platform that is movable in two dimensions over the stationary array of immunodiffusion or immunoelectrophoresis plates. That arrangement facilitates use of the scanning system as an aid to fill the antigen and antibody wells. For that purpose a digitally controlled dispenser is mounted in fixed but offset relation to the scanning device. Video signals from the scanner are supplied to the computer, which is suitably programmed to recognize the shapes of the individual wells, or to identify machine readable symbols associated with them. As the platform carrying scanner and dispenser is moved under computer control over the plates, it can then readily be stopped when the scanner axis is located accurately over a selected antigen well. The platform may then be moved a fixed increment to center the dispensing tip over the well so that the correct charge is dispensed accurately into the well.

When all wells are filled in this manner with the appropriate antigen solutions, with suitable washing of the dispenser between operations, electrophoresis is initiated. A similar loading operation is typically carried out to charge the antibody wells, either after completion of the electrophoresis, or immediately after filling the antigen wells if electrophoresis is omitted. After the desired time for diffusion the same scanning device is moved successively to all positions where zones of precipitation are to be scanned throughout the array of plates.

The scanning capability of the scanning device is preferably used also to scan the array of plates before the wells are loaded. The computer is programmed to compare the observed positions of the antigen and antibody wells, recording any departure from uniformity of dimensions or relative positions among the plates of the array. Any plate or individual well found to depart too far from standard can then be automatically omitted during the loading operation; and smaller deviations can be compensated by automatically applying suitable corrections to the parameter values that are ultimately derived by the computer.

Initial zone scanning procedure typically comprises request by the computer for video information at successive exploration addresses with a selected x value and with y values shifting progressively by a specified interval over the region in which zone formation is anticipated. The video intensity values received from register 125 are stored with x, y and t data for each explored point. After each such y-scan, the x coordinate is shifted by a specified interval and a similar y-scan is performed and the results recorded, until the entire area of interest has been covered. Each received intensity value is typically compared with the previously received and stored values. If the observed intensity variations exceed a set threshold characteristic of a background area, indicating presence of a precipitation zone, each intensity value within the zone is so designated in memory. Also, for each y-scan, the intensity maximum as the zone is crossed is identified and recorded, establishing the zone axis in terms of a series of y values at uniformly spaced x values. The end points of each zone are identified typically as the terminal x values in each direction at which an intensity maximum was identified. If more precise location of the end points is desired, the computer is instructed to perform further scans in a defined region about each end point with reduced x and y intervals.

With the existing precipitation zones so located and recorded, straightforward arithmetic operations are performed on the stored data, yielding the described intensity sum parameter $I_x$ for each cross-scan of a zone in the y direction; and addition of those values gives the total intensity parameter $I_x$ for the zone. Subtraction of the x values at the zone ends gives the parameter L. Additional parameters may be obtained by appropriate computation as desired.

The described measurements are preferably carried out as a unitary operation on a complete set of plates that includes one or more unknown samples and also a set of related standard solutions of the type discussed above and sufficiently complete to permit evaluation of the unknown samples. After each scan of such a plate set, the computer is preferably directed to derive concentration values for each of the proteins for which precipitation zones were found. If, as is preferred, multiple standard runs are included, the probable experimental error can be derived for each calculated concentration value. Computer routines for such calculations are well known. Several independent determinations are preferably made of the concentration of each protein in the sample, typically by reference to different parameters; an average is then computed, with each value weighted in the usual way according to its probable error.

If the computed probable error for that average is within the specified range for the particular sample under study, no further measurements are needed. The computer then produces a conventional printout or other record of the final results, together with as much of the original data as may be requested by the program. For example, the physician for whom the analysis is being carried out may require a complete copy of all the data on magnetic tape or the like for possible future reference. Also, photographs of the immunodiffusion plate can be taken, either directly or using the monitor tube.

Ordinarily, one cycle of scanning does not permit an adequate quantitative determination of a protein unless it is present in high concentration. After a suitable length of supplementary incubation, which may vary from a few minutes, say, to an hour or more, the above described scanning process is repeated, typically for the entire set of test plates and the corresponding standards. The computer is typically instructed to explore plate areas where zones were expected but not found during the previous scan; and also areas corresponding to the previously found and recorded precipitation zones, preferably allowing for specified expansion or movement of those zones which are set into the program on the basis of previous experience. Thus, the computer operations can maintain a continuity of treatment of the respective protein zones between one scan and the next.

Occasionally two precipitation zones due to distinct proteins are so close together that their normal growth ultimately produces overlap. For zones produced by immunoelectrophoresis, such overlap normally occurs at or near the zone ends, leading to crossing of the zones as shown typically for zones a and b of FIG. 1D. When immunodiffusion is carried out without initial fractionation, the overlap tends to be confined to the zone center portions, as when zones d and d' of that figure grow together. The computer is typically programmed to anticipate such a zone overlap, to recognize it when it has occurred, and then to make suitable modifications in the procedure used for deriving the various parameters.

When the proteins under study are such that overlaps are expected, each plate is typically scanned at an early stage of zone development before zone overlaps have occurred (FIG. 1B). The zone axis and end points can then be located without ambiguity. The computer is typically programmed as part of the regular processing of each scan to check for actual overlaps, for example by comparing the (x,y) coordinates for each measured point of a zone axis with those for the adjacent zones, coincidence within a specified threshold indicating an overlap. All scans preferably also include a check for potential overlaps. For example, the computer extrapolates each zone axis beyond the observed end points and compares the extrapolated axis points of adjacent zones. Such axis extrapolation may comprise a simple linear extension in the direction of the axis slope near each end. Alternatively, the observed zone axis may be fitted by a parabola or other curve, which can then be extrapolated accurately.

Zone overlap can also be detected by computing the rate of change of slope of the zone axis, or the radius of curvature of that axis, at a series of points along the zone. Any departure from the normally smooth variation of those functions indicates that the zone may be made up of two or more overlapping zones.

When an actual overlap is found on one half of a zone, sufficiently accurate compensation can often be made by simply replacing the observed intensity values in the area of overlap with the values observed at the corresponding points of the other half of the zone. Such correspondence between two points for zones due to immunoelectrophoresis is typically defined as equal x spacing on opposite sides of $x_g$ of the point of closest approach to the antibody well; and for zones due to direct immunodiffusion is defined as equal y spacing on opposite sides of the zone axis. The axis within the area of overlap can usually be located by extrapolation.

More elaborate and accurate compensation procedures are also available, if desired. For example, the computer is instructed to adjust the measurement at the selected symmetrically placed point of the unaffected half of the zone to take account of any actual lack of symmetry of the zone. That unsymmetry can be determined, for example, by comparing the values that were obtained for the two points during a previous scan prior to the overlap, and applying the ratio of those values as a correction factor.

A further illustrative compensation procedure takes account also of the intensity value actually measured at the region of overlap, which is due, of course, partly to one zone and partly to the other. The computer is instructed to divide that observed value at each point of overlap in an appropriate ratio. A suitable approximate ratio may be obtained by comparing measured values for the two zones at the respective symmetrically placed points already described, either with or without the described adjustment of those values.

Whenever possible, it is preferred to employ two or more distinct computation procedures for compensating for areas of overlap, averaging the results and determining the probable error. It is emphasized, however, that the region of overlap is ordinarily a small fraction of the entire area of a zone. Hence even quite appreciable errors in approximating the true value within the overlap still may not affect the final result significantly.

Also, for each of the described types of overlap, it is usually possible to make the determination of protein concentration in terms of parameters that are defined by portions of the zone not affected by the overlap. Thus, the measurements preferably employed are those near the zone center for processes similar to immunoelectrophoresis, and those near the zone ends for processes similar to direct immunodiffusion.

It will be recognized by those skilled in the art that many particulars of the described procedures can be replaced by their obvious equivalents without departing from the proper scope of the present invention. For example, values for those parameters that do not require a series of measurements at successive incubation times can be obtained from measurements made after the incubation process has been allowed to reach substantial equilibrium. Such measurements have the advantage that the zone configurations are virtually static, and the exact time of measurement is therefore not crucial. As a further example, at a desired stage of the incubation the zones of precipitation can be stained in known manner with an appropriate dye, and zone measurements can then be made using selectively transmitted light. That method of measurement is usually most useful after equilibrium has been reached, since it is then not necessary to assign a precise time of measurement.

In summary, methods have been described by which immunodiffusion, immunoelectrophoresis and analagous processes can be used to provide truly quantitative measurement of the concentrations of individual proteins in biological fluids. Actual use of the described methods has demonstrated that protein concentrations can be determined within five percent or better. The invention thus provides an effective and convenient method for making a wide variety of experimental and diagnostic determinations.

We claim:

1. Apparatus for obtaining a quantitative measure of the concentration of a protein in an antigen sample, comprising means for supporting and illuminating a plate carrying a precipitation zone due to immunoelectrophoresis of said antigen sample with an antibody specific to said protein, photoresponsive means for extracting a plurality of electrical signals representing the light intensity at positions on said plate which correspond to respective sets of position representing signals, and electronic means for supplying to said photoresponsive means sets of position representing signals corresponding to positions in selected respective spatial relationship to said zone, and for deriving from the resulting light intensity representing signals the corresponding value of a parameter which varies in characteristic manner with said protein concentration.

2. Apparatus according to claim 1 wherein said electronic means include means for supplying automatically to said photoresponsive means a series of sets of position representing signals which correspond to a two-dimensional array of positions distributed partly within and partly outside the zone, and memory means for storing the resulting light representing signals together with position signals representing the position to which each light representing signal corresponds.

3. Apparatus according to claim 1, including also means for producing a two-dimensional visual display of said light representing signals, said electronic means including manually controllable means for developing a set of position representing signals corresponding to a selected position on said display, and means for producing in digital form the light representing signal corresponding to the so developed position representing signals.

4. Apparatus for obtaining a quantitative measure of the concentration of an antigen in an antigen containing sample which has been subjected to immunodiffusion with an antibody specific to said antigen, the antigen and antibody diffusing through a supporting medium from respective sources mutually spaced along an axis and reacting to form at least one elongated precipitation zone of limited length; said apparatus comprising means for automatically scanning the supporting medium to develop electrical signals representing light intensity at respective positions of a two-dimensional array distributed partly within the zone and partly outside the zone, each light representing signal being associated with electrical position representing signals identifying the corresponding position in said array, and means responsive jointly to position representing signals and the corresponding light representing signals for deriving the value of a selected parameter of the zone which varies in characteristic manner with said antigen concentration.

5. Apparatus according to claim 4 including means for causing said scanning means to repeat said scanning action intermittently, and means for associating electrical time signals with said light representing signals.

6. Apparatus for obtaining a quantitative measure of the concentration of an antigen in an antigen containing sample by subjecting the sample to immunodiffusion with an antibody source containing an antibody specific to said antigen, said reactants diffusing in a supporting medium from respective antigen and antibody wells to produce a precipitation zone; said apparatus comprising photoresponsive means for scanning the wells and the supporting medium to develop electrical signals representing light intensity at respective positions, each light representing signal being associated with electrical position representing signals identifying the corresponding position, dispensing means for dispensing antigen and antibody containing solutions selectively to the respective wells in response to electrical command signals, and control means responsive jointly to the light representing signals and the position representing signals and having one mode of operation for producing operative position of the dispensing means relative to each individual well and for supplying a command signal to the dispensing means to supply that well with a selected reagent, said control means having another mode of operation for deriving electronically from the light representing signals and the position representing signals the corresponding value of a selected zone parameter which varies in characteristic manner with said antigen concentration.

7. Apparatus according to claim 6, said control means, when in said one mode, including means for deriving signals representing the position of each well, and being responsive to such well position signals for producing operative position of the dispensing means.

8. Apparatus according to claim 6 including
means associated with said control means, when in said one mode, for comparing the relative positions of said wells with predetermined standard relative well positions to detect deviations therefrom,
and means associated with said control means, when in said other mode, for compensating for such deviations during said parameter derivation.

* * * * *